United States Patent [19]

Maurer et al.

[11] 4,424,166

[45] Jan. 3, 1984

[54] PREPARATION OF 1,1-DIHALOGENO-ALKENES

[75] Inventors: Fritz Maurer, Wuppertal; Uwe Priesnitz, Solingen; Hans-Jochem Riebel, Wuppertal, all of Fed. Rep. of Germany

[73] Assignee: Bayer Aktiengesellschaft, Leverkusen, Fed. Rep. of Germany

[21] Appl. No.: 237,005

[22] Filed: Feb. 23, 1981

[30] Foreign Application Priority Data

Mar. 12, 1980 [DE] Fed. Rep. of Germany ....... 3009487

[51] Int. Cl.³ .................. C07C 121/48; C07C 121/66; C07C 69/743; C07C 61/35
[52] U.S. Cl. .............................. 260/464; 260/465 G; 260/465.7; 560/8; 560/21; 560/57; 560/101; 560/124; 562/435; 562/491; 562/405; 562/506; 564/166; 564/181; 564/161; 564/190; 568/314; 568/329; 568/346; 570/217
[58] Field of Search ............... 568/347, 348; 260/464, 260/465 G; 564/190; 560/124, 21, 57, 101, 8; 562/506, 435, 491, 405

[56] References Cited

FOREIGN PATENT DOCUMENTS 2849 7/1979 European Pat. Off. .

OTHER PUBLICATIONS

Fieser, et al., Reagents for Organic Synthesis, vol. 1, p. 1059 (1967).
Fieser, et al., Reagents for Organic Synthesis, (1969), vol. 2, pp. 130, 131, 132, 210, 280, 281, 379, 381, 432, 442, 443, 456, 457.
Fieser, et al., Reagents for Organic Synthesis, vol. 4, p. 83 (1974).
Allen et al., J.A.C.S., 77 (1955), pp. 2871-2875.
J. Org. Chem., 30 (1965), 1027-1029, Fuqua et al.
Fuqua et al., Tetrahedron Letters, No. 23, (1964), pp. 1461-1463.
Burton et al., Tetrahedron Letters, No. 1, (1968), pp. 71-76.

Primary Examiner—Joseph Paul Brust
Attorney, Agent, or Firm—Sprung, Horn, Kramer & Woods

[57] ABSTRACT

In the preparation of a 1,1-dihalogenoalkene of the formula $$X^1\phantom{XX}R^1$$
$$\phantom{XX}C=C$$
$$X^2\phantom{XX}R^2$$

in which
$R^1$ is a hydrogen atom or an optionally substituted alkyl, alkenyl, alkynyl, cycloalkyl, aralkyl, aralkenyl or aryl radical, and
$R^2$ is an optionally substituted alkyl, alkenyl, alkynyl, cycloalkyl, aralkyl, aralkenyl or aryl radical, or
$R^1$ and $R^2$ together form an optionally branched and/or optionally benzo-fused hydrocarbon chain, and
$X^1$ and $X^2$ each independently is a halogen atom, wherein a carbonyl compound of the formula $$O=C\begin{matrix}R^1\\R^2\end{matrix}$$

is reacted with a trihalogenoacetate of the formula $$X^2-\underset{\underset{X^3}{|}}{\overset{\overset{X^1}{|}}{C}}-COO^\ominus\ M^\oplus$$

in which
$X^3$ is a halogen atom, and
$M^\oplus$ is an alkali metal ion or one equivalent of an alkaline earth metal ion, in the presence of an approximately equimolar amount of a phosphorus-containing compound, the improvement which comprises employing as said phosphorus-containing compound a phosphorous acid trialkyl ester or a phosphorous acid triamide and effecting the reaction at a temperature between about 0° and 200° C. A preferred end product is $$\begin{matrix}Cl\\ \phantom{X}\diagdown\\ \phantom{XX}C=CH\phantom{XX}CO-OC_2H_5\\ \diagup\phantom{XXXXX}\diagdown\phantom{X}\diagup\\ Cl\phantom{XXXXXXX}\triangle\\ \phantom{XXXXXX}H_3C\phantom{X}CH_3\end{matrix}$$

and the preferred phosphorus-containing compound is trimethyl phosphite, triethyl phosphite, tripropyl phosphite or phosphorous acid tris-dimethyl-amide.

7 Claims, No Drawings

PREPARATION OF 1,1-DIHALOGENO-ALKENES

The invention relates to an unobvious process for the preparation of certain known 1,1-dihalogeno-alkenes.

It is known that certain 1,1-dihalogeno-alkenes, such as β,β-difluoro- or β-chloro-β-fluorostyrene, are obtained when carbonyl compounds, such as, benzaldehyde, are reacted with alkali metal trihalogenoacetates, such as sodium chlorodifluoroacetate or sodium fluorodichloroacetate, in the presence of triphenylphosphine (see Tetrahedron Lett. 1964, 1461; ibib. 1968, 71; and J. Org. Chem. 30 (1965), 1027).

However, the triphenylphosphine to be used in this process is a relatively expensive product. Recovery of the triphenylphosphine from the triphenylphosphine oxide formed in the reaction is associated with an unacceptably high level of expenditure. It was therefore necessary to investigate ways in which this process can be carried out in a less expensive manner.

The present invention now provides a process for the preparation of a 1,1-dihalogeno-alkene of the general formula

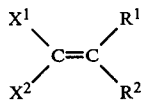

in which
R$^1$ represents a hydrogen atom or an optionally substituted alkyl, alkenyl, alkynyl, cycloalkyl, aralkyl, aralkenyl or aryl radical and
R$^2$ represents an optionally substituted alkyl, alkenyl, alkynyl, cycloalkyl, aralkyl, aralkenyl or aryl radical,
or in which
the two radicals R$^1$ and R$^2$ together represent an optionally branched and/or optionally benzo-fused hydrocarbon chain, and
X$^1$ and X$^2$ are identical or different and represent halogen atoms,
characterized in that a carbonyl compound of the general formula

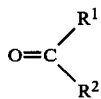

in which
R$^1$ and R$^2$ have the abovementioned meanings, is reacted with a trihalogenoacetate of the general formula

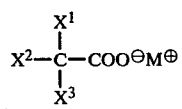

in which
X$^1$, X$^2$ and X$^3$ are identical or different and represent halogen atoms and
M$^⊕$ represents an alkali metal ion or one equivalent of an alkaline earth metal ion,
in the presence of approximately the equimolar amount of a phosphorous acid trialkyl ester (trialkyl phosphite) or of a phosphorous acid triamide, at a temperature between 0° and 200° C., optionally in the presence of a diluent.

It is surprising that 1,1-dihalogenoalkenes of the formula (I) are obtained in good yields by the process according to the invention, since it was to be expected that the reaction of carbonyl compounds with trihalogenoacetates in the presence of trialkyl phosphites or phosphorous acid triamides would proceed less selectively than when triphenylphosphine is used.

An advantage of the process according to the invention which should be mentioned is that trialkyl phosphites and phosphorous acid triamides are cheaper than triphenylphosphine. The new process is thus less expensive than the nearest synthesis method known from the state of the art.

If, for example, 3-formyl-2,2-dimethyl-cyclopropane-1-carboxylic acid methyl ester, sodium trichloroacetate and trimethyl phosphite are used as starting substances, the process of the present invention is illustrated by the following equation:

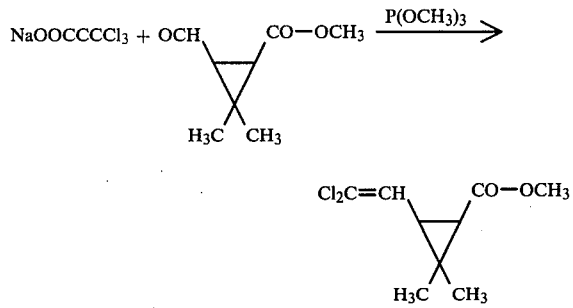

Preferred carbonyl compounds of formula (II) to be used as starting substances are those in which
R$^1$ represents a hydrogen atom, an optionally halogen-substituted C$_1$ to C$_5$ alkyl radical, an optionally halogen-substituted benzyl or phenylethyl radical, or a phenyl radical which is optionally substituted by halogen, C$_1$ to C$_4$ alkyl, C$_1$ to C$_4$ alkoxy, methylenedioxy, cyano and/or nitro, and
R$^2$ represents an optionally halogen-substituted C$_1$ to C$_5$ alkyl radical, a C$_2$ to C$_5$ alkenyl or C$_2$ to C$_5$ alkynyl radical, an optionally halogen-substituted benzyl or phenylethyl radical, a phenyl radical which is optionally substituted by halogen, C$_1$ to C$_4$ alkyl, C$_1$ to C$_4$ alkoxy, methylenedioxy, cyano and/or nitro, an optionally halogen-substituted styryl radical or a radical of the the general formula

in which
Z represents an acetyl, cyano, carbamoyl or C$_1$ to C$_4$ alkoxycarbonyl radical or a radical of the formula COOM,
in which
M represents a hydrogen atom, an alkali metal, one equivalent of an alkaline earth metal or an ammonium radical.

Particularly preferred starting substances are those compounds of the formula (II) in which $R^1$ represents a hydrogen atom and $R^2$ represents a $C_2$ to $C_5$ alkenyl radical or a radical of the general formula (IV), as given above, in which Z represents a cyano, acetyl, carboxyl, $C_1$ to $C_4$ alkoxycarbonyl radical or a radical of the formula COOM, in which M represents hydrogen, sodium or potassium.

Examples of the starting compounds of the formula (II) which may be mentioned are: β,β-dimethylacrolein, 3-formyl-2,2-dimethyl-1-cyanocyclopropane, 3-formyl-2,2-dimethyl-1-acetyl-cyclopropane, 3-formyl-2,2-dimethyl-cyclopropane-1-carboxylic acid and its sodium salt, and 3-formyl-2,2-dimethyl-cyclopropane-1-carboxylic acid methyl ester, ethyl ester, n-propyl ester, isopropyl ester, n-butyl ester, isobutyl ester, sec.-butyl ester and tert.-butyl ester.

Some of the compounds of the formula (II) are known (see Synthesis 1975, 535–536; and Tetrahedron Lett. 1976, 1979–1982): Some of the particularly preferred cyclopropane derivatives of the formula (II) have not yet been described in the literature. These compounds are obtained by processes which are in themselves known. A synthesis route is outlined in the following equation (in which R represents a $C_1$ to $C_4$ alkyl radical):

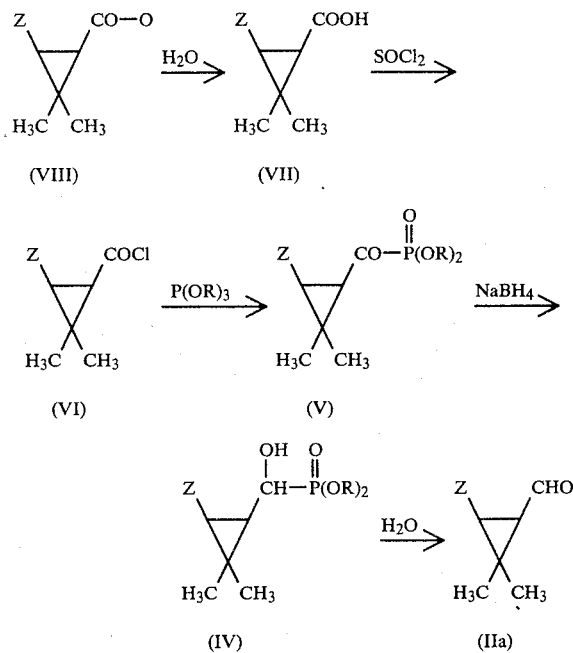

Hydrolysis of known cyclopropanecarboxylic acid esters of the formula (VIII) (see J. Org. Chem. 32, (1967), 3351–3355; Bull. Soc. Chim. Belg. 87 (1978), 721–732; and Tetrahedron Lett. 1978, 1847–1850), for example by reaction with aqueous-alcoholic potassium hydroxide solution at temperatures between 20° and 100° C. and subsequent acidification, gives the carboxylic acids of the formula (VII). These can be converted into the acid chlorides of the formula (VI) by reaction with halogenating agents, such as thionyl chloride, at a temperature between 20° and 80° C.

Reaction of the acid chlorides (VI) with trialkyl phosphites at a temperature between −20° and +150° C., preferably between 0° and 120° C., gives the cyclopropanoylphosphonic acid esters of the formula (V) (see J. Am. Chem. Soc. 86 (1964), 3862–3866; and Methoden der organischen Chemie (Methods of Organic Chemistry) (Houben-Weyl-Müller), 4th Edition, Volume 12/1, page 453, Georg-Thieme-Verlag, Stuttgart 1963). The products are isolated and purified by distillation, if necessary under reduced pressure.

The α-hydroxy-phosphonic acid esters of the formula (IV) are obtained by reducing the oxo compounds of the formula (V) with sodium tetrahydridoborate, if appropriate using a diluent, such as water or aqueous methanol, at a temperature between −20° and +50° C., the pH value being kept between 5 and 8 by adding a buffer agent, such as sodium hydrogen phosphate (see Chem. Ber. 103 (1970), 2984–2986). For working up, the mixture is extracted with a water-immiscible solvent, such as methylene chloride, the extracts are dried and filtered and the solvent is distilled off from the filtrate under reduced pressure.

The corresponding aldehydes of the formula (IIa) can be prepared from the α-hydroxy-phosphonic acid esters of the formula (IV) by treatment with sodium hydroxide solution at a temperature between 0° and 100° C., preferably between 10° and 50° C. (see Chem. Ber. 103 (1070), 2984–2986).

As an alternative to the preparation process outlined above, aldehydes of the formula (IIa) are also obtained by reacting acid chlorides of the formula (VI) with lithium tri-tert.-butoxy-hydrido-aluminate, which has been prepared, if necessary in situ, from lithium tetrahydridoaluminate and tert.-butanol, the reaction being carried out, if appropriate, in the presence of a diluent, such as tetrahydrofuran, at a temperature between −100° and +100° C., preferably between −80° and +50° C. For working up, the reaction mixture is poured into a mixture of hydrochloric acid and ice-water and extracted with a water-immiscible solvent, such as diethyl ether. The extracts are dried and filtered and the filtrate is concentrated. If necessary, the residue is distilled in order to purify the crude product.

Preferred trihalogenoacetates of formula (III) to be employed as starting substances are those in which $X^1$, $X^2$ and $X^3$ independently of one another represent a fluorine, chlorine or bromine atom, preferably a chlorine atom, and $M^\oplus$ represents a sodium or potassium ion.

Examples which may be mentioned are sodium trichloroacetate, sodium chloro-difluoroacetate and sodium fluoro-dichloroacetate.

The compounds of the formula (III) are known.

Examples which may be mentioned of the phosphorous acid trialkyl esters or phosphorous acid amides to be used in the process according to the invention are trimethyl phosphite, triethyl phosphite, tripropyl phosphite and phosphorous acid tris-dimethylamide.

The process according to the invention is preferably carried out using diluents. Possible diluents are virtually any of the inert organic solvents, in particular aprotic polar solvents. These include ethers (such as glycol dimethyl ether, diglycol dimethyl ether, tetrahydrofuran and dioxane), carboxylic acid amides (such as dimethylformamide, dimethylacetamide and N-methylpyrrolidone), sulphoxides (such as dimethylsulphoxide), phosphoric acid amides (such as hexamethylphosphoric acid triamide), and nitriles, (such as acetonitrile and propionitrile).

The reaction temperature is kept between about 0° and 200° C., preferably about 10° to 180° C., and especially about 140° to 160° C. when trialkyl phosphites are used and especially about 10° to 50° C. when phosphorous acid amides are used. The process is in general carried out under normal pressure or under a pressure corresponding to the vapor pressure of the particular diluent at the reaction temperature.

About 0.9 to 1.2 moles, preferably about 0.95 to 1.1 moles, of trihalogenoacetate of the formula (III) and of phosphorous acid ester or amide are employed per mole of carbonyl compound of the formula (II).

For carrying out the process according to the invention, when phosphorous acid trialkyl esters are used, it is preferable to mix all the reactants in a diluent at room temperature (about 20° C.) and to heat the reaction mixture to 140° to 160° C. for several hours, while stirring.

If phosphorous acid triamides are used, it is preferable initially to introduce the starting substances of the formulae (II) and (III) in a diluent and to meter in the phosphorous acid amide slowly at 10° to 50° C., after which the reaction mixture is stirred for some hours at room temperature.

Working up can be carried out by customary methods, for example by a procedure in which the reaction mixture is diluted with water and extracted with an organic solvent which is virtually immiscible with water, such as methylene chloride, the organic phase is dried and filtered and the filtrate is evaporated. The products, which remain in the residue, can be purified in the customary manner, for example by vacuum distillation.

1,1-Dihalogeno-alkenes prepared by the process according to the invention can be used as intermediate products for the preparation of insecticidally and acaricidally active pyrethroids (see DE-OS (German Published Specification) No. 2,326,077).

PREPARATIVE EXAMPLES

Example 1

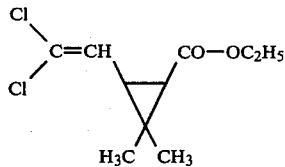

A mixture of 17.0 g (0.1 mole) of 3-formyl-2,2-dimethyl-cyclopropane-1-carboxylic acid ethyl ester, 16.6 g (0.1 mole) of triethyl phosphite and 18.5 g (0.1 mole) of sodium trichloroacetate in 100 ml of diglyme was heated to 150° C. under argon for 6 hours. The reaction mixture was then poured into water. Extraction with 2 portions of 100 ml each of methylene chloride followed. The combined methylene chloride extracts were dried over sodium sulphate. 3-(2,2-Dichlorovinyl)-2,2-dimethyl-cyclopropane-1-carboxylic acid ethyl ester was obtained as a crude product in a yield of 73% of theory.

Example 2

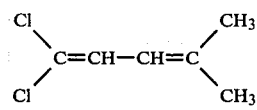

8.2 g (0.05 mole) of phosphorous acid tris-dimethylamide were added dropwise to a mixture of 9.2 g (0.05 mole) of sodium trichlororacetate, 4.2 g (0.05 mole) of β,β-dimethylacrolein and 100 ml of diethylene glycol dimethyl ether. During this addition, the temperature rose to about 45° C. The mixture was subsequently stirred for 3 hours, 200 ml of water were added and the mixture was extracted twice with 100 ml of methylene chloride each time. The combined organic phases were washed with 50 ml of 10% strength sodium hydroxide solution and 2 portions of 50 ml each of water, dried over sodium sulphate and evaporated in vacuo. The residue was distilled in vacuo. 7.3 g (77% of theory) of 1,1-dichloro-4,4-dimethylbutadiene were thus obtained in the form of a colorless liquid with a boiling point of 54°–56° C./10 mm Hg.

It will be appreciated that the instant specification and examples are set forth by way of illustration and not limitation, and that various modifications and changes may be made without departing from the spirit and scope of the present invention.

We claim:
1. A process for the preparation of a 1,1-dihalogenoalkene of the formula

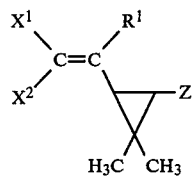

in which
R$^1$ is a hydrogen atom or an optionally halogen-substituted C$_1$ to C$_5$ alkyl radical; an optionally halogen-substituted benzyl or phenylethyl radical; or a phenyl radical which is optionally substituted by halogen, C$_1$ to C$_4$ alkyl, C$_1$ to C$_4$ alkoxy, cyano and/or nitro;
Z is an cyano or C$_1$ to C$_4$ alkoxycarbonyl radical, or a radical of the formula COOM,
M is a hydrogen atom, an alkali metal, one equivalent of an alkaline earth metal or an ammonium radical, and
X$^1$ and X$^2$ each independently is a halogen atom, consisting essentially of reacting a carbonyl compound of the formula

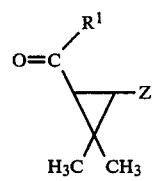

with a trihalogenoacetate of the formula

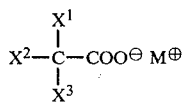

in which

X³ is halogen atom, and

M⊕ is an alkali metal ion or one equivalent of an alkaline earth metal ion, in the presence of an approximately equimolar amount of a trialkyl phosphite at a temperature between about 0° and 200° C.

2. A process according to claim 1, wherein the reaction is carried out in the presence of an aprotic polar solvent as a diluent.

3. A process according to claim 1, wherein the reaction is carried out at a temperature between about 140° and 160° C.

4. A process according to claim 1, in which
 $R^1$ is a hydrogen atom,
 Z is a cyano, carboxyl or $C_1$ or $C_4$ alkoxycarbonyl radical or a radical of the formula COOM, and
 M is sodium or potassium.

5. A process according to claim 1, in which
 $X^1$, $X^2$ and $X^3$ are chlorine atoms, and
 M⊕ is a sodium or potassium ion.

6. A process according to claim 1, in which the trialkyl phosphite is trimethyl phosphite, triethyl phosphite or tripropyl phosphite.

7. A process according to claim 4, in which
 $X^1$, $X^2$ and $X^3$ are chlorine atoms,
 M⊕ is a sodium or potassium ion,
the trialkyl phosphite is trimethyl phosphite, triethyl phosphite or tripropyl phosphite, and the reaction is carried out in the presence of an aprotic polar solvent as a diluent.

* * * * *